(12) United States Patent
Higashi et al.

(10) Patent No.: US 10,153,182 B2
(45) Date of Patent: Dec. 11, 2018

(54) SUBSTRATE PROCESSING APPARATUS

(75) Inventors: Noboru Higashi, Neyagawa (JP);
Satoru Hiraki, Neyagawa (JP); Hiromi Kiyose, Neyagawa (JP); Hideaki Sato, Koshi (JP); Hiroshi Komiya, Koshi (JP)

(73) Assignees: Kurashiki Boseki Kabushiki Kaisha, Kurashiki-shi (JP); Tokyo Electron Limited, Tokyo (JP)

( * ) Notice: Subject to any disclaimer, the term of this patent is extended or adjusted under 35 U.S.C. 154(b) by 1104 days.

(21) Appl. No.: 13/598,431

(22) Filed: Aug. 29, 2012

(65) Prior Publication Data
US 2013/0048215 A1   Feb. 28, 2013

(30) Foreign Application Priority Data
Aug. 31, 2011   (JP) .................. 2011-189159

(51) Int. Cl.
*H01L 21/67* (2006.01)
*H01L 21/311* (2006.01)
*G01N 21/3577* (2014.01)

(52) U.S. Cl.
CPC ... *H01L 21/67086* (2013.01); *G01N 21/3577* (2013.01); *H01L 21/67248* (2013.01); *H01L 21/67253* (2013.01); *H01L 21/31111* (2013.01)

(58) Field of Classification Search
CPC ................................................. G01N 21/3577
See application file for complete search history.

(56) References Cited

U.S. PATENT DOCUMENTS

| 6,353,203 | B1 * | 3/2002 | Hokodate et al. ....... 219/121.67 |
| 2002/0084416 | A1 | 7/2002 | Kiuchi |

(Continued)

FOREIGN PATENT DOCUMENTS

| JP | 11-200072 A | 7/1999 |
| JP | 2000-187143 A | 7/2004 |

(Continued)

OTHER PUBLICATIONS

Office Action received in Chinese Patent Application No. 201210311001.9, dated Sep. 28, 2014.

(Continued)

*Primary Examiner* — Karla A Moore
*Assistant Examiner* — Margaret D Klunk
(74) *Attorney, Agent, or Firm* — Knobbe, Martens, Olson & Bear, LLP (57) ABSTRACT

A substrate processing apparatus that performs processing by immersing a substrate into a processing liquid obtained by mixing phosphoric acid with a diluent includes a concentration sensing means for sensing the concentration of the processing liquid by measuring the absorbance characteristics of the processing liquid. The concentration sensing means includes a light-transmitting section that introduces the processing liquid into the inside to let the processing liquid pass therethrough, a light-emitting section that radiates light having a predetermined wavelength to the light-transmitting section, a light-receiving section that receives the light therefrom via the light-transmitting section, a first lens that condenses the light emitted from the light-emitting section to the light-transmitting section, a second lens that condenses the light that has passed through the light-transmitting section to the light-receiving section, and a cooling mechanism that cools at least one of these.

4 Claims, 8 Drawing Sheets

(56) References Cited

U.S. PATENT DOCUMENTS

| | | |
|---|---|---|
| 2004/0140365 A1 | 6/2004 | Izuta |
| 2004/0157452 A1* | 8/2004 | Ogawa et al. ............... 438/691 |
| 2005/0067101 A1 | 3/2005 | Funabashi |
| 2006/0028633 A1* | 2/2006 | Takami ............... G03F 7/70891 |
| | | 355/67 |
| 2007/0248127 A1 | 10/2007 | Shiraishi |
| 2008/0308530 A1 | 12/2008 | Izuta |
| 2011/0315228 A1 | 12/2011 | Yokota |
| 2013/0240143 A1* | 9/2013 | Kiyose et al. ........... 156/345.15 |

FOREIGN PATENT DOCUMENTS

| | | |
|---|---|---|
| JP | 2004-22154 A | 8/2004 |
| JP | 2004-221540 A | 8/2004 |
| JP | 2005-072251 A | 3/2005 |
| JP | 2005-079212 A | 3/2005 |
| JP | 2009-058306 A | 3/2009 |
| TW | 200741366 A | 11/2007 |
| TW | 201044130 A | 12/2010 |

OTHER PUBLICATIONS

Notice of Preliminary Rejection dated Sep. 16, 2013 in corresponding Korean Patent Application No. 10-2012-0090973.
Office Action dated Nov. 21, 2014 in corresponding JP Application No. 2011-189159.
Office Action dated Aug. 3, 2015 in corresponding TW Application No. 101128605.

* cited by examiner

SUBSTRATE PROCESSING APPARATUS

CROSS-REFERENCE TO RELATED APPLICATIONS

This application claims priority to Japanese Patent Application No. 2011-189159 filed on Aug. 31, 2011, the disclosure of which, including the specification, the drawings, and the claims, is hereby incorporated by reference in its entirety.

BACKGROUND OF THE INVENTION

Field of the Invention

The present invention relates to a substrate processing apparatus that performs processing of a substrate such as a semiconductor wafer, a glass substrate for a liquid crystal display device, or a glass substrate for a photomask (hereafter simply referred to as "substrate") with a processing liquid and, in particular, is useful as a technique of performing concentration control while sensing the concentration of the processing liquid at a high precision when immersing and processing the substrate in the processing liquid that has been heated to a high temperature.

Description of the Related Art

Conventionally, as a substrate processing apparatus of this kind, there is known, for example, a substrate processing apparatus that performs an etching treatment of a silicon nitride film (SiN) on a substrate surface using a high-temperature solution of phosphoric acid ($H_3PO_4$).

For example, in the case of etching a silicon nitride film with a phosphoric acid solution in a semiconductor wafer process, it is general that a silicon oxide film ($SiO_2$) is present on the substrate surface in addition to the silicon nitride film. In such a case, the object of etching is only the silicon nitride film, and it is generally demanded that the silicon oxide film is hardly etched by the processing liquid.

As a mechanism by which the silicon nitride film and the silicon oxide film are etched with a phosphoric acid solution, it is known that the silicon nitride film is etched by water in the phosphoric acid solution, and the silicon oxide film is etched by phosphoric acid in the phosphoric acid solution.

For this reason, in order to manage the etching amount of the silicon nitride film with a good precision, the concentration of the processing liquid, that is, the ratio of mixing a chemical agent liquid with a diluent, and the temperature of the processing liquid are extremely important. Also, generally, in a phosphoric acid solution at a high temperature, the amount of evaporation of water which is the diluent is large, so that concentration control by replenishment with water is important. As a substrate processing apparatus equipped with means for holding the temperature or concentration of the processing liquid to be constant, apparatus disclosed in JP-A-11-200072 and JP-A-2004-221540 are known.

For example, in JP-A-11-200072, there is disclosed a substrate processing apparatus that performs automatic control of the replenishment rate of water in accordance with a result of comparison between the current temperature and the boiling temperature of a phosphoric acid bath which is used as a set temperature in performing concentration control of the phosphoric acid bath by replenishment with water. In this apparatus, what is actually controlled is only the temperature of the processing liquid, and this is means for replenishment with the diluent that is dependent on the physical phenomenon that the concentration of the processing liquid does not become the boiling concentration or below.

However, in the case of the apparatus disclosed in JP-A-11-200072, since the phosphoric acid bath concentration corresponding to the boiling temperature of the phosphoric acid bath is constant, the concentration and the temperature of the processing liquid are simultaneously determined when the etching rate of the silicon nitride film is determined, thereby raising a problem in that the two cannot be independently adjusted. Also, there is a need to perform the replenishment so that the amount of replenishment with the diluent will be slightly larger than the original amount of evaporation; however, when the amount of replenishment becomes excessive, it will be a cause of decrease in the temperature of the processing liquid or bumping of the processing liquid.

Also, JP-A-2004-221540 discloses a substrate processing apparatus that includes temperature controlling means for operating the heating means so that the temperature of the processing liquid will be the set temperature, replenishment means for replenishing the processing tank with the diluent so as to adjust the concentration of the processing liquid, concentration sensing means for sensing the concentration of the processing liquid by the specific weight of the processing liquid or the like, and concentration controlling means for adjusting the amount of replenishment with the diluent so that the sensed concentration of the processing liquid will be a little higher than the boiling temperature.

However, in the case of the apparatus disclosed in JP-A-2004-221540, the concentration sensing means converts the pressure of the gas supplied from the sensing end within the processing tank to the specific weight of the processing liquid, so that the pressure of the gas supplied from the sensing end changes in accordance with the temperature of the processing liquid, the amount of liquid within the processing tank, and the flow of the processing liquid within the processing tank. Therefore, the sensing must be carried out under conditions such that the temperature of the processing liquid, the amount of liquid within the processing tank, and the flow within the processing tank are constant. However, in actual use, when the processing liquid is replenished with the diluent in order to control the concentration of the processing liquid, the temperature of the processing liquid also changes, thereby raising a problem in that a correct concentration cannot be determined until the temperature of the processing liquid returns to the set temperature.

Also, JP-A-2009-58306 discloses a concentration measuring method that calculates the concentration of metal ions in an aqueous solution of phosphoric acid by gradually lowering the temperature of the aqueous solution, optically sensing the change in transmittance by deposition of insoluble components, and determining the concentration of the metal ions from the deposition temperature, as well as an etching apparatus equipped with a reproduction system using the same.

SUMMARY OF THE INVENTION

However, in the case of the concentration measuring method disclosed in JP-A-2009-58306, a step of gradually lowering the temperature of the aqueous solution will be needed, so that the concentration measurement could not be carried out in real time though the method is an optical sensing method.

Therefore, the present applicants have developed a substrate processing apparatus that can perform independent concentration control because the concentration of the processing liquid can be directly sensed by an optical sensing method, and have filed a patent application (Patent Application No. 2010-166288 which had not been laid open to public yet at the time of filing the present application).

However, according to the studies made by the present inventors, it has been found out that, in sensing the concentration of a processing liquid by an optical sensing method in a substrate processing apparatus that performs etching with a high-temperature phosphoric acid solution, the lenses disposed in the neighborhood undergo temperature change by radiation heat from the measurement cell, so that measurement errors occur by being affected therefrom.

Here, the fact that, in a concentration measuring apparatus using an optical sensing method, the lenses disposed in the neighborhood undergo temperature change by radiation heat from the measurement cell and measurement errors occur by being affected therefrom, and the countermeasures against this have not been known up till now.

Therefore, an object of the present invention is to provide a substrate processing apparatus that can perform independent concentration control because the concentration of the processing liquid can be directly sensed and, moreover, processing of the substrate with a chemical agent can be carried out with a good precision because measurement errors caused by temperature change of the lenses are hardly generated.

The aforementioned object can be achieved by the present invention such as the following.

The substrate processing apparatus of the present invention, is a substrate processing apparatus comprising:

a processing tank that stores a processing liquid obtained by mixing phosphoric acid with a diluent and performs processing by immersing a substrate into the processing liquid;

heating means for heating the processing liquid;

replenishing means for replenishing the processing liquid with the diluent;

concentration sensing means for sensing a concentration of the processing liquid by measuring absorbance characteristics of the processing liquid; and concentration controlling means for operating the replenishing means so that the concentration sensed by the concentration sensing means may come close to a set concentration, wherein the concentration sensing means comprises:

a light-transmitting section that introduces the processing liquid into an inside to let the processing liquid pass therethrough;

a light-emitting section that radiates light having a predetermined wavelength to the light-transmitting section;

a light-receiving section that receives the light from the light-emitting section via the light-transmitting section;

a first lens that is disposed between the light-emitting section and the light-transmitting section to condense the light emitted from the light-emitting section to the light-transmitting section;

a second lens that is disposed between the light-transmitting section and the light-receiving section to condense the light that has been emitted from the light-emitting section and has passed through the light-transmitting section to the light-receiving section; and a cooling mechanism that performs cooling of at least one of the first lens and the second lens.

According to the substrate processing apparatus of the present invention, the concentration sensing means directly senses the concentration of the processing liquid by measuring the absorbance characteristics of the processing liquid, so that an independent concentration control can be made with little influence given from the temperature of the processing liquid. Further, since the concentration sensing means includes a cooling mechanism that cools the lenses, measurement errors caused by temperature change of the lenses are hardly generated, whereby the concentration of the processing liquid can be sensed with a higher precision, so that the processing of the substrate with a chemical agent can be carried out with a good precision. Also, for example, even when the temperature of the processing liquid lowers by immersion of a substrate wafer, replenishment with water or stoppage for maintaining the concentration of the processing liquid can be made and, as a result, the etching of the silicon nitride film will be stabilized. Also, according to the present invention, the ratio of mixing the chemical agent with the diluent can be freely controlled within a range above or equal to the boiling point concentration of the chemical agent, so that, for example, by setting the concentration of the phosphoric acid solution to be higher than the boiling point concentration, the amount of etching the silicon nitride film can be reduced and the amount of etching the silicon oxide film can be increased.

In the present invention, it is preferable to further comprise a first lens holding section that holds the first lens and a second lens holding section that holds the second lens, wherein the cooling mechanism performs the cooling via at least one of the first lens holding section and the second lens holding section. By this feature, the lenses can be indirectly cooled via the lens holding sections, so that the efficiency and the uniformity of cooling can be enhanced. Also, since the cooling mechanism is provided in the first and second lens holding sections, not only the lenses but also the first and second lens holding sections themselves can be cooled. As a result thereof, the deformation and dilatation of the lens holding sections by heat can be prevented, whereby the position of holding the lenses can be maintained to be a constant position, so that the phosphoric acid concentration can be measured at a high precision.

It is preferable that the cooling mechanism comprises a flow path disposed in the first lens holding section or the second lens holding section and means for supplying a cooling fluid to the flow path. By this feature, the lenses can be cooled efficiently by the cooling fluid supplied to the lens holding sections.

In the embodiment, it is preferable that the flow path is disposed in the first lens holding section or the second lens holding section to surround all or a part of peripheries of the first lens or the second lens. By this feature, the cooling fluid can be supplied to the part of the lens holding sections that surround the lenses, so that the efficiency and the uniformity of cooling can be enhanced to a greater extent.

Also, it is preferable to further comprise a base section that supports the first lens holding section and the second lens holding section, wherein a cooling mechanism is provided in the base section. By cooling the base section, the influence of deformation caused by heat of the base section can be prevented, and also the influence of heat directly transmitted to the lens holding sections via the base section from the flowcell section can be reduced, so that the concentration measurement can be made at a higher precision.

Also, it is preferable to further comprise temperature sensing means for sensing a temperature of the processing liquid and temperature controlling means for operating the heating means so that the temperature sensed by the temperature sensing means may come close to a set temperature. By this feature, the temperature control can be made separately from the concentration control because the temperature sensing means senses the temperature of the processing liquid and the temperature controlling means operates the heating means.

BRIEF DESCRIPTION OF THE DRAWINGS

FIGS. 6A and 6B are views illustrating one example of an essential part of the substrate processing apparatus of the present invention, where

DETAILED DESCRIPTION OF THE PREFERRED EMBODIMENTS

A substrate processing apparatus of the present invention is used, for example, in heating a processing liquid obtained by mixing phosphoric acid with a diluent and performing a treatment by immersing a substrate into this processing liquid. In the present embodiment, description will be given by adopting, as an example, an apparatus in which the processing liquid is a phosphoric acid solution containing phosphoric acid as a chemical agent liquid and water as a diluent, and an etching treatment is carried out by immersing a substrate (for example, a silicon wafer for semiconductor) into this phosphoric acid solution while heating the solution.

Figure 1:
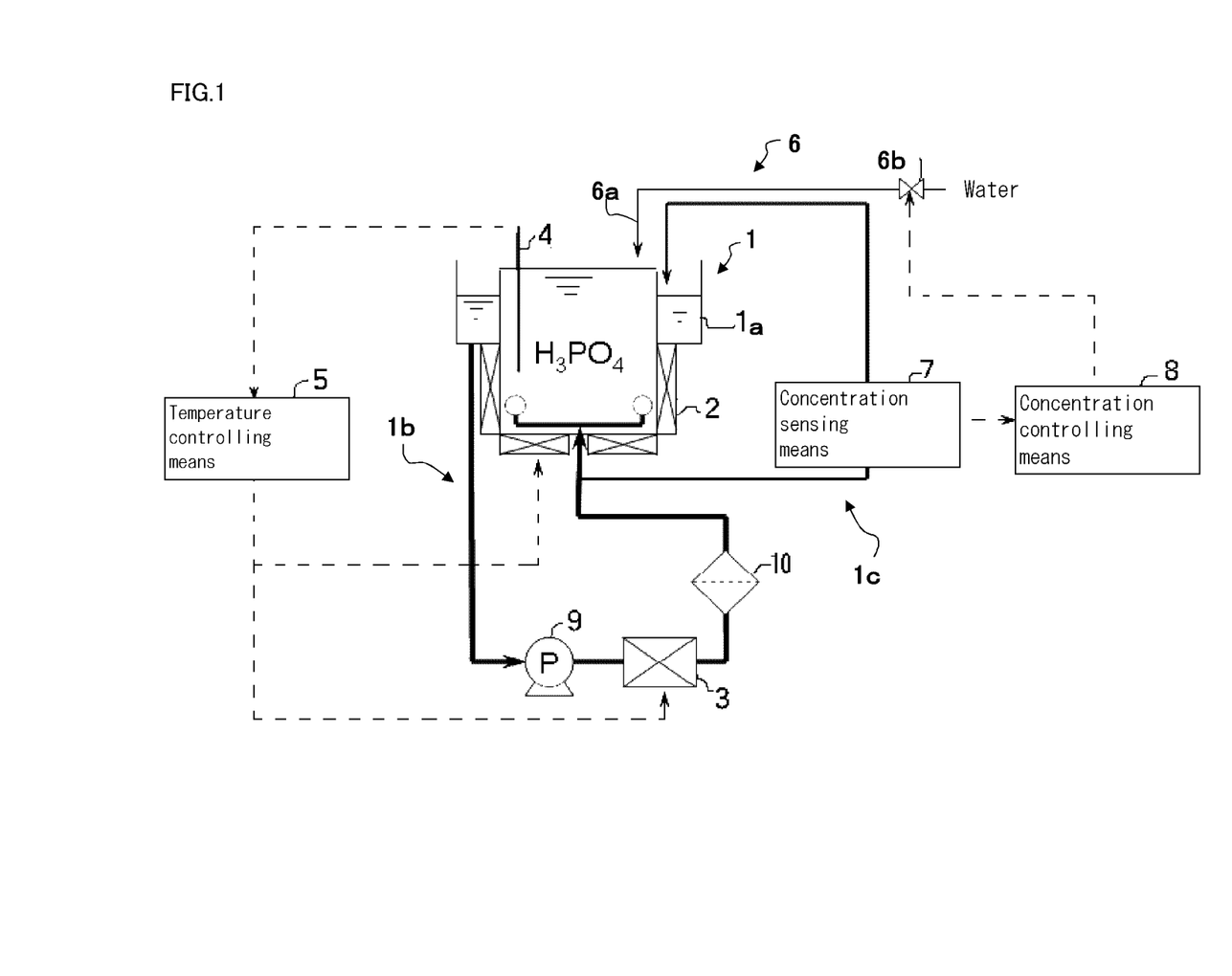
FIG. 1 is a schematic construction view illustrating one example of a substrate processing apparatus of the present invention.

This substrate processing apparatus includes a processing tank 1 that performs a treatment by immersing a substrate into a processing liquid obtained by mixing phosphoric acid with a diluent while storing the processing liquid. In the present embodiment, as shown in FIG. 1, an example is shown in which a collection tank 1a for collecting the phosphoric acid solution overflowed from the processing tank 1 is disposed in the peripheries of the processing tank 1. The phosphoric acid solution collected in the collection tank 1a is returned to the processing tank 1 via a circulation pipe 1b.

The above-described circulation pipe 1b is provided with a circulation pump 9, heating means 3, and a filter 10, and is connected to an eruption pipe disposed at the bottom part of the processing tank 1.

An electric heater or the like is used as the heating means 3. The filter 10 is used to remove particles from the phosphoric acid solution returned to the processing tank 1. The filter 10 is, for example, a porous membrane or the like made of a fluororesin or the like.

Around the processing tank 1 and the collection tank 1a, heating means 2 for heating the phosphoric acid solution in the tanks are disposed, and an electric heater or the like is used therefor. The heating means 3 of the circulation pipe 1b and the heating means 2 for the tanks correspond to the heating means in the present invention. Heating by the heating means is carried out, for example, at 110° C. or higher.

A top part of the processing tank 1 may be provided with a cover that is freely openable and closable. A plurality of substrates served as an object of processing are held in an upright posture at an equal interval by a holding arm that is freely ascendable and descendable. When the holding arm is outside of the tank, the cover is closed. When a group of substrates are put into the tank while being held by the holding arm, the cover is opened. While an etching treatment is carried out after the group of substrates are put into the tank, the cover is closed again.

The collection tank 1a and the like are provided with a phosphoric acid supplying section (not illustrated in the drawings) for supplying phosphoric acid. Also, the processing tank 1 is provided with a water replenishment section 6a for replenishing with water such as pure water. The water replenishment section 6a is provided with a nozzle disposed in the fringe neighborhood of the processing tank 1, a pipe that connects this nozzle in communication with a water supplying source, and a flow rate regulating valve 6b that intervenes in the pipe. These correspond to the replenishment means in the present invention.

In the present embodiment, an example is shown in which temperature sensing means 4 that senses the temperature of the phosphoric acid solution is disposed in the processing tank 1. As the temperature sensing means 4, a temperature sensor using a thermocouple or the like is used. A sense signal obtained by the temperature sensing means 4 is sent to temperature controlling means 5. On the basis of this sense signal, the temperature controlling means 5 operates the heating means 2, 3 so that the sensed temperature may come close to a set temperature. As the control at that time, a PID (proportion, integration, differentiation) control, an ON/OFF control, or the like can be made. Specifically, the temperature controlling means 5 performs control by operating the heating means 2, 3 so that the temperature of the phosphoric acid solution will be, for example, within a range from 159 to 161° C.

Figure 2:
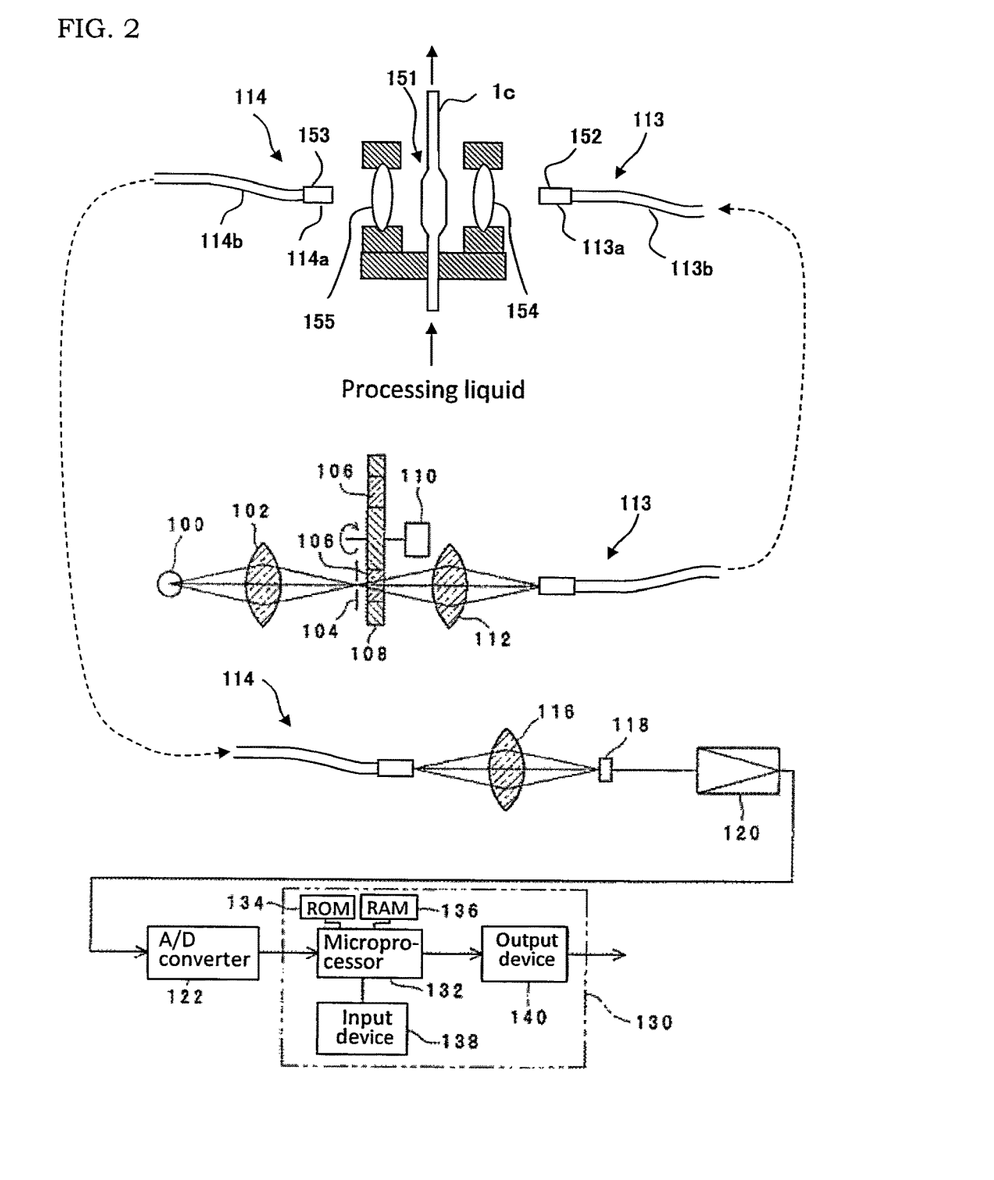
FIG. 2 is a schematic construction view illustrating one example of an essential part of a substrate processing apparatus of the present invention.
Figure 6:
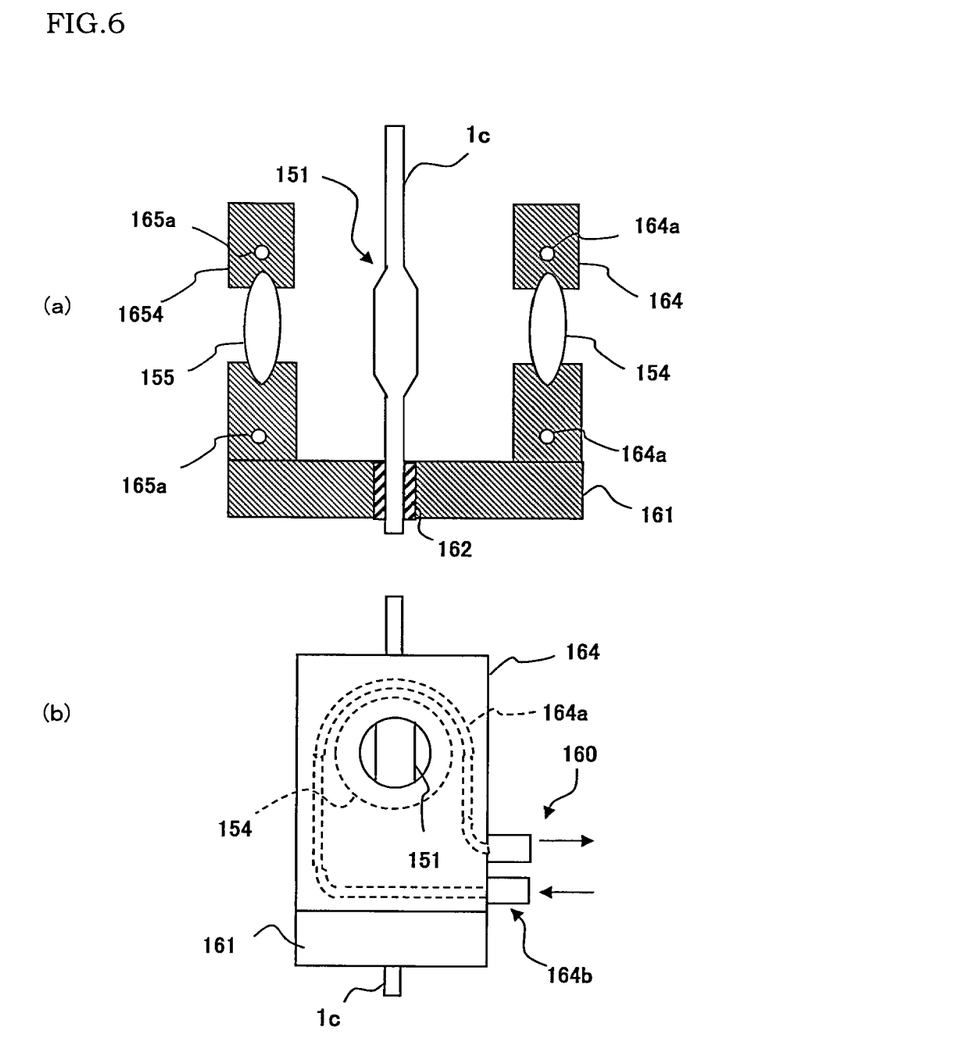
FIG. 6A is a longitudinal cross-sectional view and FIG. 6B is a right side view.

Referring to FIG. 1, the substrate processing apparatus of the present invention includes concentration sensing means 7 that senses the concentration of a processing liquid by measuring the absorbance characteristics of the processing liquid. Referring to FIG. 2 or 6, this concentration sensing means 7 includes a light-transmitting section 151 that introduces the processing liquid into an inside to let the processing liquid pass therethrough, a light-emitting section 152 that radiates light having a predetermined wavelength to the light-transmitting section 151, a light-receiving section 153 that receives the light from the light-emitting section 152 via the light-transmitting section 151, a first lens 154 that is disposed between the light-emitting section 152 and the light-transmitting section 151 to condense the light emitted from the light-emitting section 152 to the light-transmitting section 151, a second lens 155 that is disposed between the light-transmitting section 151 and the light-receiving section 153 to condense the light that has been emitted from the light-emitting section 152 and has passed through the light-transmitting section 151 to the light-receiving section 153, and a cooling mechanism 160 that performs cooling of at least one of the first lens 154 and the second lens 155.

Referring to FIG. 6, in the present embodiment, an example is shown in which the first lens 154 and the second lens 155 are held by a first lens holding section 164 and a second lens holding section 165, and the cooling mechanism 160 is provided for cooling the first lens 154 and the second lens 155 indirectly by cooling the first lens holding section 164 and the second lens holding section 165. In the present invention, it is preferable that the cooling mechanism 160 performs the cooling via at least one of the first lens holding section 164 and the second lens holding section 165 in this manner.

As a material of the first lens holding section 164 and the second lens holding section 165, it is preferable to use an inorganic material in view of heat conductivity when these are provided with the cooling mechanism 160, and it is more preferable to use a metal such as aluminum, copper, stainless steel, or invar (nickel-iron alloy).

In the illustrated example, the first lens 154 and the second lens 155 are held directly by the first lens holding section 164 and the second lens holding section 165 in order to enhance the cooling efficiency. This is because, when a material having a poor heat conductivity such as rubber or resin intervenes, the temperature of the lenses is liable to rise. Here, in view of holding the lenses with a good precision while enhancing the cooling efficiency, the first lens 154 and the first lens holding section 164 are preferably in contact with each other with an area of 5 to 30%, more preferably with an area of 10 to 30%, relative to the total surface area of the lenses. This applies in the same manner to the relationship between the second lens 155 and the second lens holding section 165.

Flow paths 164a, 165a are provided in the first lens holding section 164 and the second lens holding section 165. The cooling mechanism 160 is provided with means for supplying a cooling fluid to the flow paths 164a, 165a. The means for supplying a cooling fluid may be simply means for supplying service water, ion-exchange water, pure water, or the like (in this case, the cooling fluid is discharged to the outside of the system after use); however, means for circulating the liquid that has been cooled below or equal to a predetermined temperature may be provided. The temperature of the cooling fluid may be a temperature that can lower the temperature of the lenses; however, the temperature of the cooling fluid is preferably 30° C. or below, more preferably 20° C. or below.

As the cooling mechanism 160 of a type that performs circulation, one that is provided with means for transporting liquid such as a pump, a circulation pipe, and a heat exchanger for cooling the cooling fluid (typically, a heat exchanger constituting a freezing cycle) can be exemplified. The circulation pipe and the like are connected to a flow path connection section 164a of the first lens holding section 164. The same applies to the second lens holding section 165.

In the present invention, it is preferable that the flow path 164a, 165a that allows the cooling fluid to move and flow is disposed in the first lens holding section 164 or the second lens holding section 165 to surround all or a part of the peripheries of the first lens 154 or the second lens 155. In the illustrated example, 50% or more of the whole circumference of the lenses is surrounded by the flow path 164a, 165a; however, it is preferable that 80% or more of the whole circumference of the lenses is surrounded by the flow path 164a, 165a.

Also, in the present embodiment, an example is shown in which the first lens holding section 164 and the second lens holding section 165 are supported by and integrated with a base section 161, and this base section 161 holds the light-transmitting section 151 via a branched pipe 1c. The base section 161 may be made of the same material as that of the first lens holding section 164 and the second lens holding section 165; however, in order to insulate the heat from the branched pipe 1c, it is preferable to use resin, ceramics, or the like. When metal is used as a material of the base section 161, it is preferable to adopt a structure in which the branched pipe 1c is held via a heat-insulating material 162 made of rubber, resin, or the like, as shown in the illustrated example.

The first lens 154 and the second lens 155 are preferably made of a material that is hardly affected by heat and may be made, for example, of quartz, sapphire, or glass. As the light-transmitting section 151, any of the cells made of quartz, sapphire, glass, transparent resin, or the like can be used; however, quartz is preferable. The degree of light condensation by the first lens 154 and the second lens 155 is determined by the area of light radiation to the processing liquid serving as an object of measurement.

In fixing the first lens holding section 164 and the second lens holding section 165 to the base section 161, a fixation position adjustment mechanism for adjusting the focal distance or focal position of the lenses may be provided. Similarly, in holding the light-transmitting section 151 or the branched pipe 1c to the base section 161, a fixation position adjustment mechanism for adjusting the fixation position of the light-transmitting section 151 or the branched pipe 1c may be provided.

The concentration sensing means 7 is for sensing the concentration of the processing liquid by measuring the absorbance characteristics of the processing liquid. The absorbance characteristics can be measured by an intensity value of the light transmitted through the processing liquid. Specifically, the concentration of acid in a phosphoric acid solution can be determined by introducing the phosphoric acid solution serving as an object of measurement into the light-transmitting section, allowing light having a different wavelength to be transmitted through the light-transmitting section, measuring an intensity value of the transmitted light, calculating the absorbance from the intensity value, and using the absorbance and a calibration line formula.

The calibration line formula can be determined as a calibration line formula between the absorbance and the acid concentration in the phosphoric acid solution by introducing a sample of a phosphoric acid solution having a known concentration into a cell or the like for light transmittance, allowing light having a different wavelength in an infrared wavelength region to be transmitted through the cell or the like, measuring an intensity value of the transmitted light, repeating this measurement for a plurality of samples, and calculating the absorbance from the intensity value of the above plurality of samples.

Further, information on the properties specific to the light-transmitting section can be incorporated into the calibration line by preparing the calibration line formula by introducing into the light-transmitting section that is put to use instead of preparing the calibration line formula by using a specific cell. Therefore, the concentration of the processing liquid can be sensed continuously without generating time lag or temperature difference by measuring the concentration directly in the circulation path of the processing liquid or the branched path thereof.

In the present invention, it is preferable that a measurement section of the concentration sensing means 7 is disposed in the light-transmitting section 151 provided in the circulation pipe 1b that is connected to the processing tank 1 or the branched pipe 1c that is branched from the circulation pipe 1b. In the present embodiment, an example is shown in which the measurement section of the concentration sensing means 7 is disposed in the light-transmitting section 151 of the branched pipe 1c that is branched from the circulation pipe 1b.

When the measurement section of the concentration sensing means 7 is disposed in the light-transmitting section 151 provided in the circulation pipe 1b that is connected to the processing tank 1 or the branched pipe 1c that is branched from the circulation pipe 1b, limitation on the material of the light-transmitting section 151 and the like can be reduced. Also, reality can be increased from the viewpoint of both the time lag and the temperature difference of measurement as compared with a case in which the sample is bypassed to a cell in the inside of the concentration measuring apparatus, whereby the precision of sensing the concentration of the processing liquid circulating within the processing tank 1 can be enhanced to a greater extent. As a result, treatment of the substrate with the chemical agent can be carried out with a better precision.

Referring to FIG. 2, for example, the concentration sensing means 7 preferably includes a light-transmitting section 151 for light transmittance to which a phosphoric acid solution serving as an object of measurement is introduced, a light source that radiates light having a wavelength in an infrared wavelength region, a light-receiving means that senses a light intensity at different wavelengths of the transmitted light obtained by radiating light from the light source, a storage means that stores a calibration line formula showing a relationship between the concentration of acid in the phosphoric acid solution and the absorbance, and a concentration calculating means for calculating the absorbance from a light intensity signal that is output from the light-receiving means and determining the concentration of acid in the phosphoric acid solution from the absorbance on the basis of the calibration line formula.

As the light source, a lamp 100 such as a tungsten lamp or a halogen lamp that generates infrared light having a wavelength around 800 to 1600 nm is used. For measurement, infrared light having a wavelength of 800 to 2000 nm, preferably 800 to 1600 nm, is used. The reason why this wavelength region is used is that the change in the amount of absorption relative to the change in the water concentration and the change in the water temperature in the phosphoric acid solution can be measured at a good precision. For example, the absorption band of water around 980 nm is observed as a change in the magnitude of absorption thereof relative to the change in the water concentration, and is observed as a shift in the absorption peak relative to the change in the water temperature. Therefore, by simultaneously measuring the absorption characteristics at a wavelength around 980 nm and at a wavelength around 1100 nm, the absorbance characteristics by water concentration and the absorbance characteristics by water temperature can be distinguished.

The infrared light radiated from the infrared lamp 100 is condensed by a first convex lens 102 and passes through an aperture 104 disposed at a focal position of the first convex lens 102 and an interference filter 106. A rotary circular disk 108 holds a plurality (for example, eight sheets) of interference filters 106 at an equal angular interval in the circumferential direction and is rotated and driven at a predetermined rotation number (for example, 1000 rpm) by a driving motor 110. Here, the interference filters 106 disperse the infrared light that has passed through the aperture 104 into infrared light having a predetermined wavelength within the aforesaid wavelength region. The infrared light that has been dispersed by the interference filters 106 is condensed by a second convex lens 112 and is introduced to an entrance terminal of an optical fiber 113 for light projection.

Details of an infrared spectroscopy apparatus using an optical fiber are disclosed in JP-A-06-11442. The optical fiber 113 for light projection includes a light-projecting head 113a (corresponding to the light-emitting section 152) on the exit side of an optical fiber 113b. Also, an optical fiber 114 for light reception includes a light-receiving head 114a (corresponding to the light-receiving section 153) on the entrance side of an optical fiber 114b.

The light-transmitting section 151 may be a flow cell connected to a pipe; however, a light-transmitting pipe can be used as it is. Quartz that is generally used as a material of a cell is liable to be etched when the processing liquid is phosphoric acid, or is liable to generate haze due to adhesion of a silicon compound dissolved in the processing liquid. Therefore, in the present invention, it is preferable to use a pipe made of a light-transmitting resin. As such a light-transmitting resin constituting the pipe, a fluororesin such as PFA is preferable in view of the chemical resistance, heat resistance, adhesion of silicon compounds, and the like. When a pipe made of a light-transmitting resin is used as the light-transmitting section 151, the degree of light condensation by the lens is preferably a diameter of about half of the diameter of the pipe serving as a cell.

In the present invention, by using a flow cell or a pipe as the light-transmitting section 151, the concentration measurement can be made continuously in line. Part of the infrared light radiated to the light-transmitting section 151 is absorbed by the phosphoric acid solution, and the rest is transmitted through the light-transmitting section 151. The infrared light that has been transmitted through the light-transmitting section 151 and introduced into the optical fiber 114 for light reception is guided out from an exit terminal of the optical fiber 114 for light reception. The light that has been guided out is condensed by a third convex lens 116 and is let to be incident into a light-receiving element 118.

When the rotary circular disk 108 is rotated and driven by the driving motor 110, the light-receiving element 118 generates a signal that is proportional to the degree of transmittance, corresponding to the phosphoric acid solution, of each infrared light corresponding to the transmittance wavelength of a plurality of interference filters 106 that are held by the rotary circular disk 108. The light-receiving element 118 converts the incident infrared light into a photocurrent corresponding to the intensity thereof.

The interference filters 106 that are held by the rotary circular disk 108 respectively have transmission wavelengths that are different from each other in accordance with the object of measurement. When the rotary circular disk 108 rotates, each of the interference filters 106 is sequentially inserted into the optical axes of the first convex lens 102 and the second convex lens 112. Then, after being dispersed by the interference filters 106, the infrared light radiated from the infrared lamp 100 is transmitted through a sample in the light-transmitting section 151 (part thereof is absorbed) and is condensed by the third convex lens 116 to be incident into the light-receiving element 118.

By this, the light-receiving element 118 outputs an electric signal corresponding to the light intensity of the infrared light of each wavelength. An amplifier 120 amplifies a transmitted light intensity signal of the light-transmitting section 151 that has been output from the light-receiving element 118. An A/D converter 122 converts an analog signal that has been output from the amplifier 120 into a digital signal.

Next, a concrete construction of a data processing section 130 will be described. The data processing section 130 receives the transmitted light intensity signal which is a digital signal from the A/D converter 122 and calculates the absorbance of the infrared light of each wavelength therefrom. Then, the concentration of water or phosphoric acid in the phosphoric acid solution is calculated on the basis of the calculated absorbance of the infrared light of each wavelength and the calibration line formula that is stored beforehand.

The calibration line formula is determined in advance by measuring the absorbance of the light of a plurality of wavelengths on a plurality of samples having a known concentration and using a multiple-order polynomial of the absorbance including a constant term between the absorbance and the concentration of each component by the multiple variable analysis method, and is stored in a storage device (RAM 136).

After being amplified by the amplifier 120, each of the signals generated by the light-receiving element 118 is converted into a digital signal by the A/D converter 122, and input into a microprocessor 132 of the data processing section 130. The data processing section 130 may be, for example, a personal computer having a microprocessor 132. The microprocessor 132 is connected to a ROM 134 that stores programs and the like, a RAM 136 serving as a work area, an input device 138 such as a keyboard or a mouse for inputting data and various commands, an output device 140 for outputting a signal to the outside, and the like. The ROM 134 stores a program or the like for operating the microprocessor 132. The RAM 136 stores the calibration line formula and various data. The microprocessor 132 calculates the absorbance at each wavelength from the input digital signal, and calculates the concentration of the phosphoric acid solution from the calculated absorbance of the light of each wavelength using the calibration line formula. The output device 140 may be a printer, a display, a data-outputting interface, or the like that outputs a result of data processing.

Figure 4:
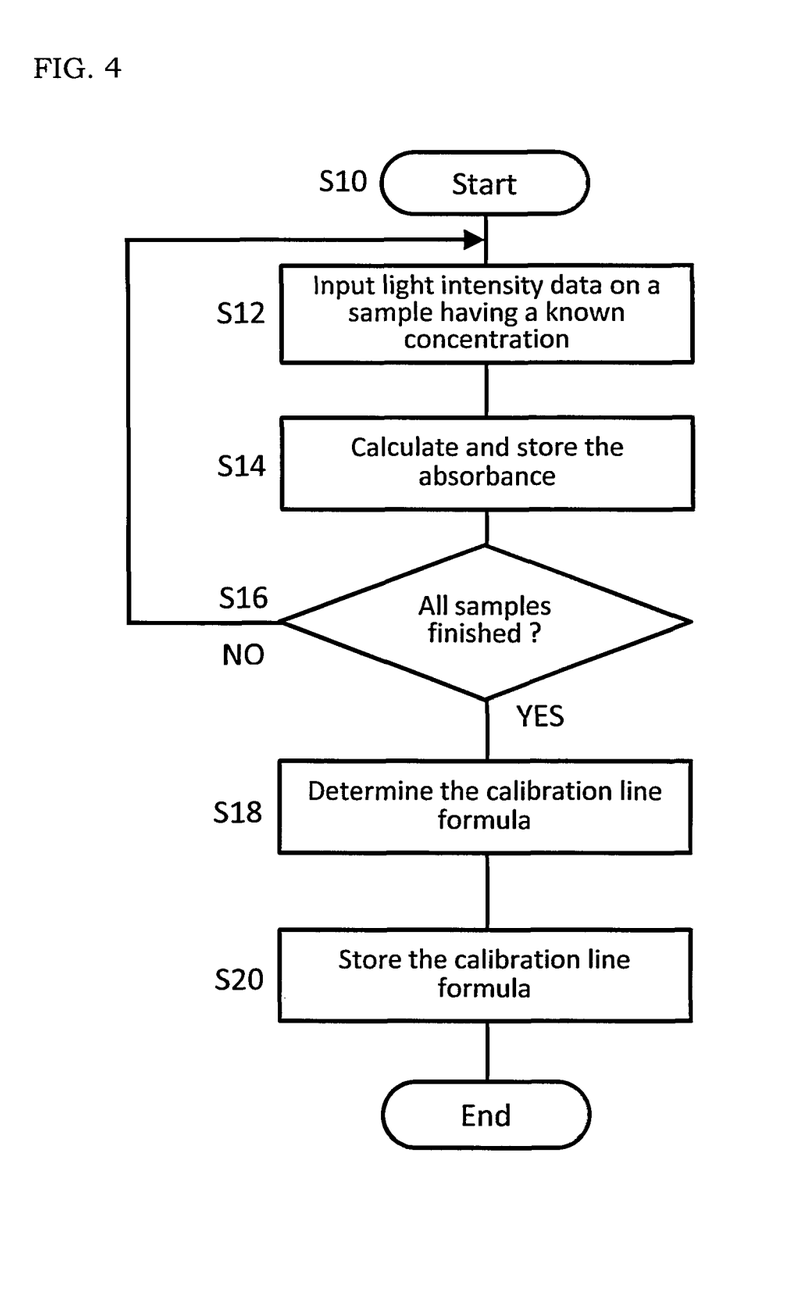
FIG. 4 is a flowchart of data processing by a microprocessor.
Figure 5:
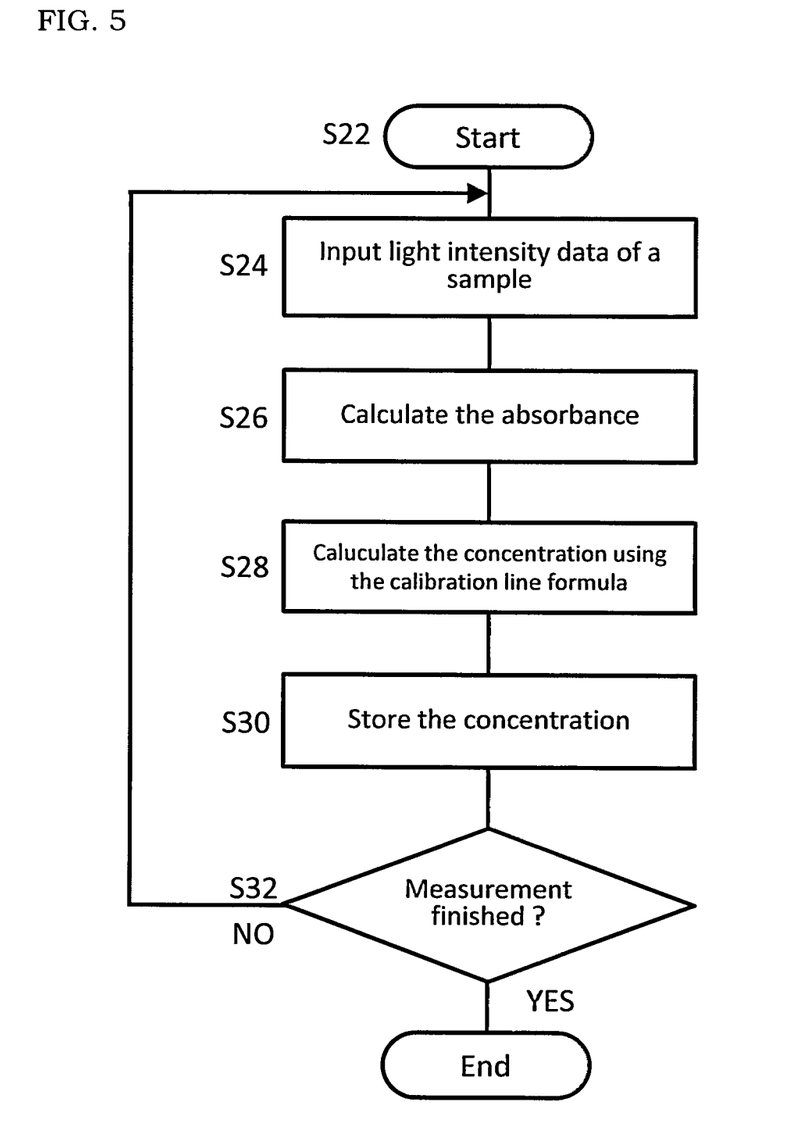
FIG. 5 is a flowchart of data processing by a microprocessor.

FIGS. 4 and 5 show a flow of processing by the microprocessor 132. First, when measurement of a sample having a known concentration is started (S10), light intensity data at a plurality of wavelengths are input from the A/D converter 122 of the optical measurement system in synchronization with the rotation of the rotary circular disk 108 (S12). Then, the absorbance is calculated from the light intensity data and stored (S14). When there is a next sample having a known concentration (YES in S16), the above-described processing is repeated. When there is no next sample having a known concentration (NO in S16), a calibration line formula between the absorbance and the concentration is calculated (S18), and stored in the RAM 136 (S20).

When measurement of a sample having an unknown concentration is started (S22), light intensity data at a plurality of wavelengths are input from the A/D converter 122 of the optical measurement system in synchronization with the rotation of the rotary circular disk 108 (S24). Then, the absorbance is calculated from the light intensity data (S26). Then, the concentration is calculated from the absorbance and the calibration line formula (S28), and stored in the RAM 136 (S30). Here, whether the measurement is ended or not is determined (S32). When the measurement is not ended, the procedure returns to the step S24, and the concentration measurement is continued.

The technique of processing the light intensity data in the processing by the microprocessor 132 shown in FIG. 4 is similar to the one disclosed in JP-A-06-265471 filed by the present applicant and used in spectroscopy measurement in the near infrared wavelength region. Concrete contents of the data processing will be described below.

First, calculation processing by the next formula (1) is carried out on the input digital signal of the light intensity, so as to calculate the absorbance $A_i$.

$$A_i = -\log_{10}(R_i - D_i)/(B_i - D_i)$$ [Formula 1]

In this formula, i is the order or number (for example, 1 to 8) of the plurality of dispersed infrared wavelengths; $R_i$ is the transmittance intensity value of the infrared light of the i-th wavelength of the phosphoric acid solution serving as an object of measurement; $B_i$ is the transmittance intensity value of the infrared light of the i-th wavelength of the phosphoric acid solution having a standard concentration that has been introduced into the light-transmitting section 151; and $D_i$ is the transmittance intensity value of the infrared light of the i-th wavelength when the light-transmitting section 151 is shielded against light. Here, $B_i$ and $D_i$ are data measured in advance and are stored in the RAM 136 of the data processing apparatus.

Next, conversion of the following formula (2) is carried out on the absorbance $A_i$ obtained by the calculation process of the formula (1).

$$S_i = A_i - A_{i+1}$$ [Formula 2]

The reason why the conversion of the formula (2) is carried out is as follows. The absorbance Ai calculated by the formula (1) undergoes change in accordance with the fluctuation of the light emission intensity of the infrared lamp 100, the sensitivity fluctuation of the light-receiving element 11, and the strain of the optical system. However, this change does not have much wavelength dependency, and is superposed with the same phase and at the same level on each of the absorbance data on the infrared light of each wavelength. Therefore, by taking a difference between the wavelengths as shown in the formula (2), this change can be cancelled.

The absorbance Ai may fluctuate by refractive index fluctuation or increase in the turbidity in accordance with the temperature fluctuation or deterioration of the phosphoric acid solution itself; however, these fluctuations can be removed by a known method. In the present invention, it is preferable that the concentration sensing means 7 performs temperature correction of the sensed concentration on the basis of the temperature of the processing liquid. In particular, it is preferable that the concentration sensing means 7 senses the concentration from which the error fluctuation caused by the temperature of the processing liquid is removed by measuring the absorbance characteristics at a plurality of wavelengths. Information on the temperature in performing the temperature correction is not separately needed when reflected on the calibration line formula. However, separate temperature sensing means may be provided near the measurement section of the concentration sensing means 7 or the like place, and the temperature correction can be made by using this.

The signal on the sensed concentration of the phosphoric acid solution obtained in the concentration sensing means 7 is sent to the concentration controlling means 8. The concentration controlling means 8 adjusts the amount of replenishment with water by operating the flow rate adjustment valve 6b of the replenishment means 6 so that the concentration sensed by the concentration sensing means 7 may come close to the set concentration. Specifically, the concentration controlling means 8 operates the flow rate adjustment valve 6b by the PID (proportion, integration, differentiation) control on the basis of the sensed concentration of the phosphoric acid solution. For example, control is made in such a manner that, when the sensed concentration of the processing liquid is above the set concentration, replenishment with the diluent is made, whereas when the sensed concentration of the processing liquid is below the set concentration, replenishment with the diluent is stopped.

In the present invention, a main controlling section for managing the whole of the substrate processing apparatus may be provided. Specifically, the main controlling section can give a command of the set temperature of the phosphoric acid solution to the temperature controlling means 5, a command of a target concentration of the phosphoric acid solution to the concentration controlling means 8, a command for operating the flow rate adjustment valve for adjusting the flow rate of phosphoric acid, and the like.

Next, an operation of the substrate processing apparatus will be described. First, the flow rate adjustment valve for adjusting the flow rate of phosphoric acid is opened, whereby the phosphoric acid is supplied to the collection tank 1a. The phosphoric acid supplied to the collection tank 1a is heated by the heating means 3 while being sent to the processing tank 1 via the circulation pipe 1b, and the phosphoric acid introduced into the processing tank 1 is heated also by the heating means 2.

The temperature of the phosphoric acid in the processing tank 1 is sensed by the temperature sensing means 4, and a signal thereof is sent to the temperature controlling means 5. The temperature controlling means 5 performs temperature management, for example, within a range of ±1° C. relative to the set temperature of 160° C. Specifically, when the liquid temperature is lower than 159° C., heating by the heating means 2, 3 is continued. When the temperature exceeds 161° C., heating by the heating means 2, 3 is stopped, and the liquid temperature is lowered by natural cooling.

The concentration of the processing liquid guided from within the processing tank 1 to the circulation pipe 1b and the branched pipe 1c is sequentially sensed by the concentration sensing means 7. The concentration controlling means 8 replenishes the processing tank 1 with water by operating the flow rate adjustment valve 6b by PID control or the like so that this sensed concentration may come close to a target concentration that is set in advance. This target concentration is set to be a little higher than the boiling point concentration corresponding to the set temperature of the phosphoric acid solution or to be a concentration higher than that concentration.

When the sensed concentration of the phosphoric acid solution in the processing tank 1 exceeds the target concentration range, replenishment with water is continued. When the sensed concentration is lower than the target concentration range, replenishment with water is stopped. When replenishment with water is stopped, water in the phosphoric acid solution is evaporated by heating of the phosphoric acid solution, whereby the concentration of the phosphoric acid solution naturally rises.

When the phosphoric acid solution in the processing tank 1 comes into the target concentration range and is stabilized, the group of substrates held by the holding arm is put into the processing tank 1, and an etching treatment of the group of substrates is started. The temperature control and the concentration control are repeatedly carried out until a predetermined processing time passes. When the processing time passes, the group of substrates are pulled up from within the tank and transported to the next processing tank.

Figure 3:
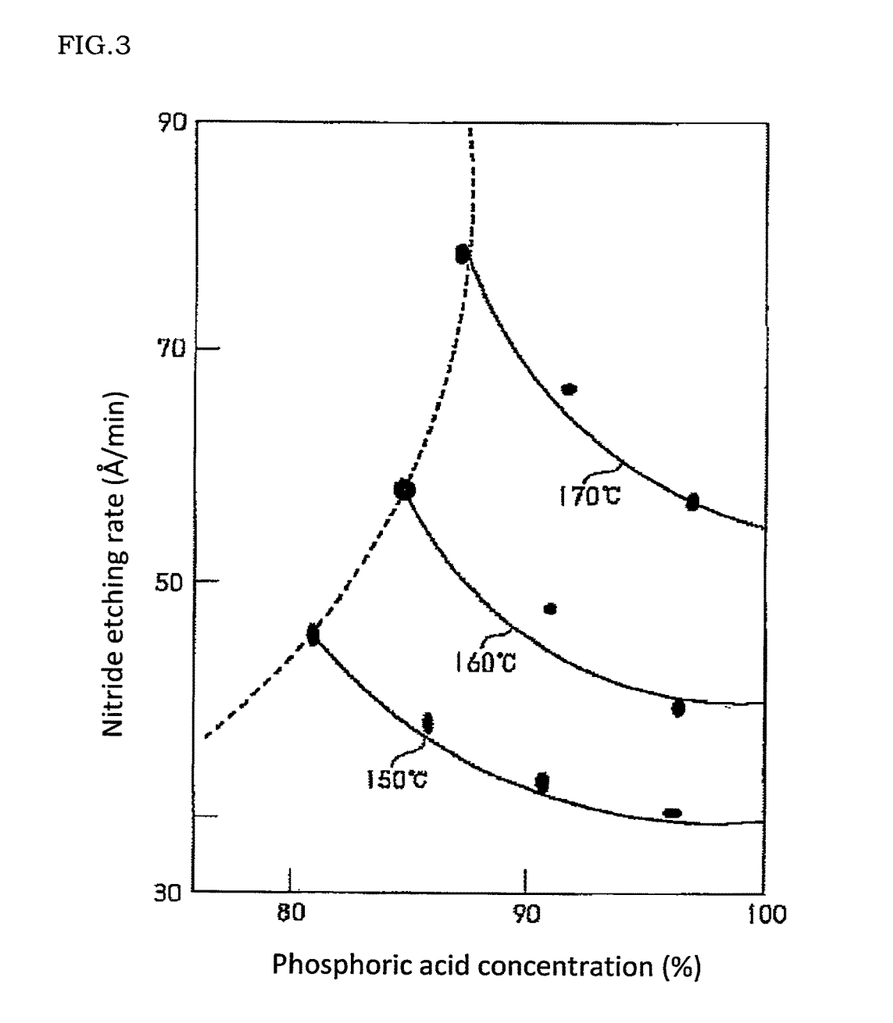
FIG. 3 is a graph depicting a relationship between the concentration and temperature of a phosphoric acid solution and the silicon nitride film etching rate.

Next, a relationship between the temperature control and the concentration control of the phosphoric acid solution in the present invention will be described with reference to FIG. 3. FIG. 3 is a graph depicting a relationship between the concentration and temperature of the phosphoric acid solution and the silicon nitride film etching rate. In this Figure, the etching rate at each temperature is shown in a solid line as an etching rate curve, and the boiling point that changes by concentration change is shown in a broken line as a boiling point curve. As shown in this Figure, the boiling point of the phosphoric acid solution has a property of rising according as the concentration of the phosphoric acid solution rises.

Also, in the present invention, the temperature controlling means 5 performs control so as to maintain the temperature of the phosphoric acid solution to be constant. Therefore, the silicon nitride film etching rate moves along the etching rate curve for each temperature in accordance with a fluctuation of the concentration. Here, cases with a temperature of 150° C., a temperature of 160° C., and a temperature of 170° C. are shown. In the previous control, the set temperature of the phosphoric acid solution is 160° C., so that the etching rate can be changed along the corresponding curve by changing the set value of concentration.

At that time, bumping of the phosphoric acid solution by replenishment with water can be prevented in advance by raising the set value of the concentration of the phosphoric acid solution to be higher than the boiling point at the set temperature. Also, for a technique of etching a silicon oxide film simultaneously with a silicon nitride film, the etching selectivity ratio of silicon nitride and silicon oxide film can be freely controlled.

OTHER EMBODIMENTS

The present invention is not limited to the above-described embodiments, so that the embodiments can be modified as follows.

(1) In the above-described embodiments, an example of a case in which the cooling mechanism is provided in the lens holding section so as to perform indirect cooling has been shown; however, in the present invention, the lenses can be directly cooled. In this case, cooling can be made by using a cooling gas. As the cooling gas, cool air (low-temperature air), low-temperature nitrogen gas, or the like can be supplied to the lenses, and a nozzle or the like for supplying the cooling gas is disposed close to the lenses as a cooling mechanism.

(2) In the above-described embodiments, an example of a case in which the cooling mechanism is provided in the lens holding section has been shown; however, the cooling mechanism can be provided in the base section, or the cooling mechanism can be provided both in the lens holding section and in the base section. When the cooling mechanism is provided in the base section, a metal is preferably used as a material thereof. As the cooling mechanism provided in the base section, one similar to that of the lens holding section can be adopted. Here, when the cooling mechanism is provided in the lens holding section, a construction may be adopted in which the cooling mechanism is provided only in one of the first and second lens holding sections.

(3) In the above-described embodiments, an example of a cooling mechanism in which the cooling is carried out by supplying a cooling fluid has been shown; however, the cooling can be made by using a cooling member such as a Peltier element without using a cooling fluid. In that case, the cooling member may be provided directly in the surroundings of the lenses or may be provided in the lens holding section.

(4) In the above-described embodiments, an example of a case in which the measurement section of the concentration sensing means is disposed in the light-transmitting section of the branched pipe that is branched from the circulation pipe connected to the processing tank has been shown; however, the light-transmitting section may be provided in the circulation pipe connected to the processing tank to dispose the measurement section.

(5) In the above-described embodiments, an example of a case in which the measurement section of the concentration sensing means is disposed at a position located away from the optical system of the concentration sensing means by using an optical fiber for light projection and an optical fiber for light reception has been shown; however, the optical system may be disposed close to the light-transmitting section of the pipe.

(6) In the above-described embodiments, an example of a case in which the concentration sensing means performs the measurement of sensed concentration by using a calibration line formula reflecting the temperature information and without being affected by the temperature of the processing liquid has been shown; however, the concentration controlling means may perform temperature correction of the sensed concentration on the basis of the temperature of the processing liquid. In that case, for example, a table that records a correction value for the sensed concentration at each temperature may be stored in advance, and an operation to calculate the correction value based on the sensed temperature may be carried out using the table. Also, a correction value of the sensed concentration at the sensed temperature can be calculated by using a function for correction that has been prepared in advance.

(7) In the above-described embodiments, an example of a case in which the concentration sensing means performs the property correction of sensed concentration on the basis of the property of the light-transmitting section in which the measurement section is disposed has been shown; however, the concentration controlling means may perform property correction of the sensed concentration on the basis of the property of the light-transmitting section. In that case, for example, a table that records a correction value for the sensed concentration for each material (material, thickness, or the like) may be stored in advance, and an operation to calculate the correction value based on the property may be carried out using the table. Also, a correction value of the sensed concentration for each property can be calculated by using a function for correction that has been prepared in advance.

(8) In the above-described embodiments, an example of a case in which the temperature sensing means senses temperature with a temperature sensor using a thermocouple has been shown; however, the absorbance characteristics of the processing liquid may be used as the temperature sensing means. In that case, separate temperature sensing means for sensing the temperature of the processing liquid by measuring the absorbance characteristics of the processing liquid may be provided; however, it is preferable that the concentration sensing means is used commonly as the temperature sensing means. In that case, the absorbance of processing liquids having a known concentration but having different temperatures may be measured in advance and added to the calibration line, so as to calculate both the concentration and the temperature of the processing liquid.

EXAMPLES

Experiments such as the following were conducted in order to study and confirm the effects of the present invention.

Experiment Example 1 (Influence of Optical Characteristics Change by Temperature Rise of the Lens)

Figure 7:
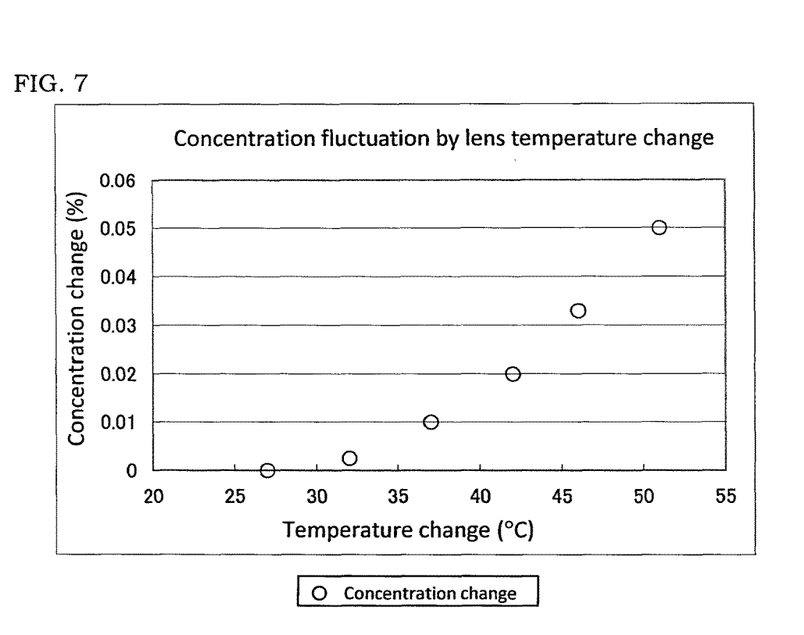
FIG. 7 is a graph depicting a change in the concentration measured in Experiment Example 1.

With use of an experiment apparatus having an optical system shown in FIG. 6, how the measurement value of zero % concentration changes in accordance with the change in the lens temperature from 25° C. in a thermostatic chamber set at 25° C. was examined without using a cell for measurement. Adjustment of the optical axis of the optical system was made using a laser so that the axial shift would be 1 mm or less at a point distant by 2 m. At the time of measurement, by changing the temperature of warm water supplied (flow rate of 1.9 L/minute) to the flow path each by 5° C. from 30° C. to 50° C., the temperature of the lens at that time was measured, and also the change in the concentration (%) corresponding to each temperature was measured using an apparatus shown in FIG. 2. The result thereof is shown in FIG. 7.

As will be clear from this result, it has been confirmed that, when the lens temperature rises by 10° C. or higher from room temperature (25° C.), greater measurement errors occur. For this reason, the temperature rise of the lens is preferably restrained to be 15° C. or less in order to suppress the concentration fluctuation caused by temperature rise of the lens or the lens holding section to be 0.03 wt % or less.

Experiment Example 2 (Influence of Optical Axis Change by Temperature Rise of the Lens Holding Section)

Figure 8:
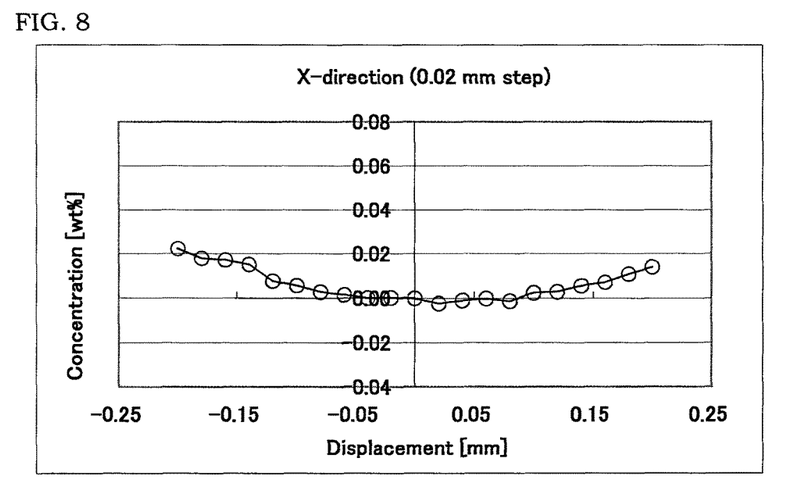
FIG. 8 is a graph depicting a change in the concentration measured in Experiment Example 2.

By using an experiment apparatus being capable of constructing an optical system shown in FIG. 6 and further having a fixed position adjustment section (XYZ stage) relative to one of the lens holding sections, how the measurement value of zero % concentration changes in accordance with the change in temperature from 25° C. in a thermostatic chamber set at 25° C. was examined without using a cell for measurement. Adjustment of the optical axis of the optical system was made using a laser so that the axial shift at the basis position would be 1 mm or less at a point distant by 2 m. At the time of measurement, the fixed position was adjusted each in the horizontal direction X (−0.2 mm to 0.2 mm) perpendicular to the optical axis, in the height direction Y (−0.2 mm to 0.2 mm), and in the horizontal direction Z (−1.0 mm to 12.5 mm parallel to the optical axis from the standard position (position at which all of XYZ are 0 mm), and the change in the concentration (%) corresponding to each position was measured by using an apparatus shown in FIG. 2. The result thereof is shown in FIG. 8.

From this result, the following points have been made clear. In order that the concentration fluctuation caused by optical axis shift from the standard position may reach 0.02 wt %, it is necessary that the shift in the optical axis is 0.2 mm or more in the XY plane.

In the case with the height (Y direction) of the lens holding section being 10 cm and a linear expansion coefficient of aluminum ($23\times10^{-6}$ [1/° C.]), the fluctuation per 1° C. is 0.0023 mm/° C., so that a temperature rise of 85° C. or more will be needed in order that the above concentration fluctuation may occur. Therefore, it has been determined that the cause of errors that must be suppressed is the temperature characteristics of the lens rather than the axial shift.

Experiment Example 3 (Influence of Cooling by Cooling Water)

Figure 9:
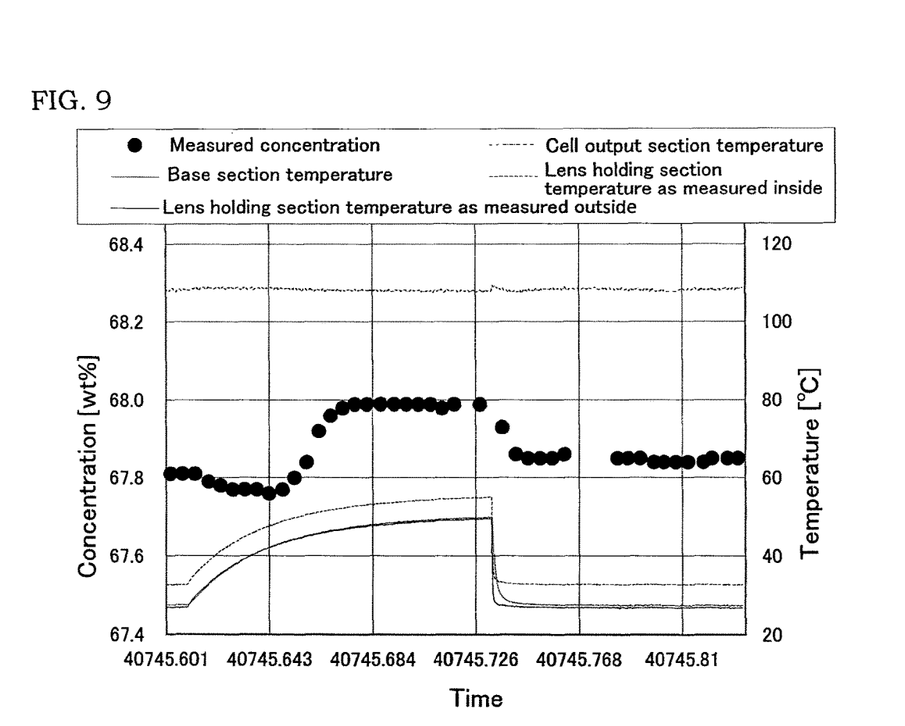
FIG. 9 is a graph depicting a change in the concentration and temperature measured in Experiment Example 3.

By using an experiment apparatus having an optical system shown in FIG. 6 and using a quartz cell for measurement, how the measurement value of concentration changes by presence or absence of cooling water was examined while allowing an aqueous solution of phosphoric acid having a temperature of 120° C. and a concentration of 67.80 wt % to flow (flow rate of 1.5 L/minute). Adjustment of the optical axis of the optical system was made using a laser so that the axial shift would be 1 mm or less at a point distant by 2 m. At the time of measurement, the temperature of each section was continuously measured, and also the change in the concentration (%) at each time was measured using an apparatus shown in FIG. 2. The result thereof is shown in FIG. 9. Here, the dots in the Figure show measurement values of concentration. As the temperature of each section, the measurement values in the inside (cell side) and on the outside (optical fiber side) of the first lens holding section 164, at the cell holding part of the base section 161, and at the exit part of the cell are shown.

As will be clear from this result, it has been confirmed that the temperature of the lens rises by about 25° C. by stopping the cooling water, whereby the concentration changes by about 0.2 wt %. Also, it has been confirmed that, when cooling with water is started again, the concentration almost returns to its original value. For this reason, it has been found out that cooling the lens is important in suppressing the measurement errors caused by temperature change.

What is claimed is:

1. A substrate processing apparatus comprising:
   a processing tank that stores a processing liquid obtained by mixing phosphoric acid with a diluent and performs processing by immersing a substrate into the processing liquid;
   a heater for heating the processing liquid;
   replenishing means for replenishing the processing liquid with the diluent;
   a concentration sensor for sensing a concentration of the processing liquid by measuring absorbance characteristics of the processing liquid; and
   concentration controller for operating the replenishing means so that the concentration sensed by the concentration sensor can come close to a set concentration,
   wherein the concentration sensor comprises:
   a light-transmitting section that introduces the processing liquid into an inside to let the processing liquid pass therethrough;
   a light-emitting section that radiates light led by an optical fiber having a predetermined wavelength to the light-transmitting section;
   a light-receiving section that receives the light from the light-emitting section via the light-transmitting section to introduce into an optical fiber;
   a first lens that is disposed between the light-emitting section and the light-transmitting section to condense the light emitted from the light-emitting section to the light-transmitting section;
   a second lens that is disposed between the light-transmitting section and the light-receiving section to condense the light that has been emitted from the light-emitting section and has passed through the light-transmitting section to the light-receiving section;
   a cooling mechanism that performs cooling of at least one of the first lens and the second lens; and
   a first lens holding piece that directly holds the first lens and a second lens holding piece that directly holds the second lens,
   wherein the cooling mechanism comprises a flow path disposed in the first lens holding section or the second lens holding section, and a supply of a cooling fluid in fluid communication with the flow path, and
   the flow path is disposed in a space within the first lens holding piece or the second lens holding piece and the space surrounds at least part of a periphery of the first lens or the second lens.

2. The substrate processing apparatus according to claim 1, wherein the space surrounds all of the periphery of the first lens or the second lens.

3. The substrate processing apparatus according to claim 1, further comprising a base section that supports the first lens holding piece and the second lens holding piece, wherein a cooling mechanism is provided in the base section.

4. The substrate processing apparatus according to claim 1, further comprising a thermometer for sensing a temperature of the processing liquid and a thermostat for operating the heater so that the temperature sensed by the thermometer can come close to a set temperature.

* * * * *